US00PP27287P3

(12) United States Plant Patent
Van Dijk

(10) Patent No.: US PP27,287 P3
(45) Date of Patent: Oct. 18, 2016

(54) ***ANTHURIUM* PLANT NAMED 'ANTHDUNDAL'**

(50) Latin Name: ***Anthurium andreanum* L.**
Varietal Denomination: ANTHDUNDAL

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 35 days.

(21) Appl. No.: 14/544,292

(22) Filed: Dec. 19, 2014

(65) Prior Publication Data

US 2016/0183438 P1 Jun. 23, 2016

(51) Int. Cl.
*A01H 5/02* (2006.01)

(52) U.S. Cl.
USPC ..... Plt./365

(58) Field of Classification Search
USPC ..... Plt./365
CPC ..... A01H 5/02
See application file for complete search history.

(56) References Cited

PUBLICATIONS

Anthura *Anthurium:* Cut flower and pot plant culture, published Nov. 2014, pp. 31 and 47.
EU Community Plant Variety Rights, Official Gazette, 1.2013, Feb. 15, 2013, pp. 27 and 44.
EU Community Plant Variety Rights application No. 2012/2605, filed Nov. 19, 2012.
EU Community Plant Variety Rights grant No. 38407, issued Jun. 16, 2014.
www.newplantandflowers.com/four-new-pot-anthuriums/;Jun. 3, 2014; 2 pages.

*Primary Examiner* — Kent L Bell
(74) *Attorney, Agent, or Firm* — Jondle & Associates, P.C.

(57) ABSTRACT

A new and distinct variety of *Anthurium* plant named 'ANTHDUNDAL' particularly characterized by having bright red, cordate spathes, white, short spadix, very rich shoot formation, a very compact plant habit and dark green foliage, is disclosed.

3 Drawing Sheets

Genus and species: *Anthurium andreanum* L.
Variety denomination: 'ANTHDUNDAL'.

BACKGROUND OF THE NEW PLANT

The present invention comprises a new and distinct variety of *Anthurium*, botanically known as *Anthurium andreanum* L., and hereinafter referred to by the variety name 'ANTHDUNDAL'. The new variety originated from a hybridization made in January 2006 in Bleiswijk, The Netherlands. The female parent is a red *Anthurium* pot plant designated '4110-03' (unpatented), and the male parent was a red *Anthurium* plant designated '5442-01' (unpatented).

A single plant was selected from the progeny of the stated cross in February 2007 and has been asexually reproduced repeatedly by tissue culture in Bleiswijk, The Netherlands over a seven-year period. The present invention has been found to retain its distinctive characteristics through successive asexual propagations.

Plant Breeder's Rights for this variety have been applied for in Europe on Nov. 19, 2012. 'ANTHDUNDAL' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands.

1) Bright red, cordate spathe;
2) White, short spadix;
3) Very rich shoot formation;
4) Very compact plant habit; and
5) Dark green foliage.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 45-week old plant grown in a greenhouse in Bleiswijk, The Netherlands in 2014.

DESCRIPTION OF THE NEW VARIETY

Figure 1:
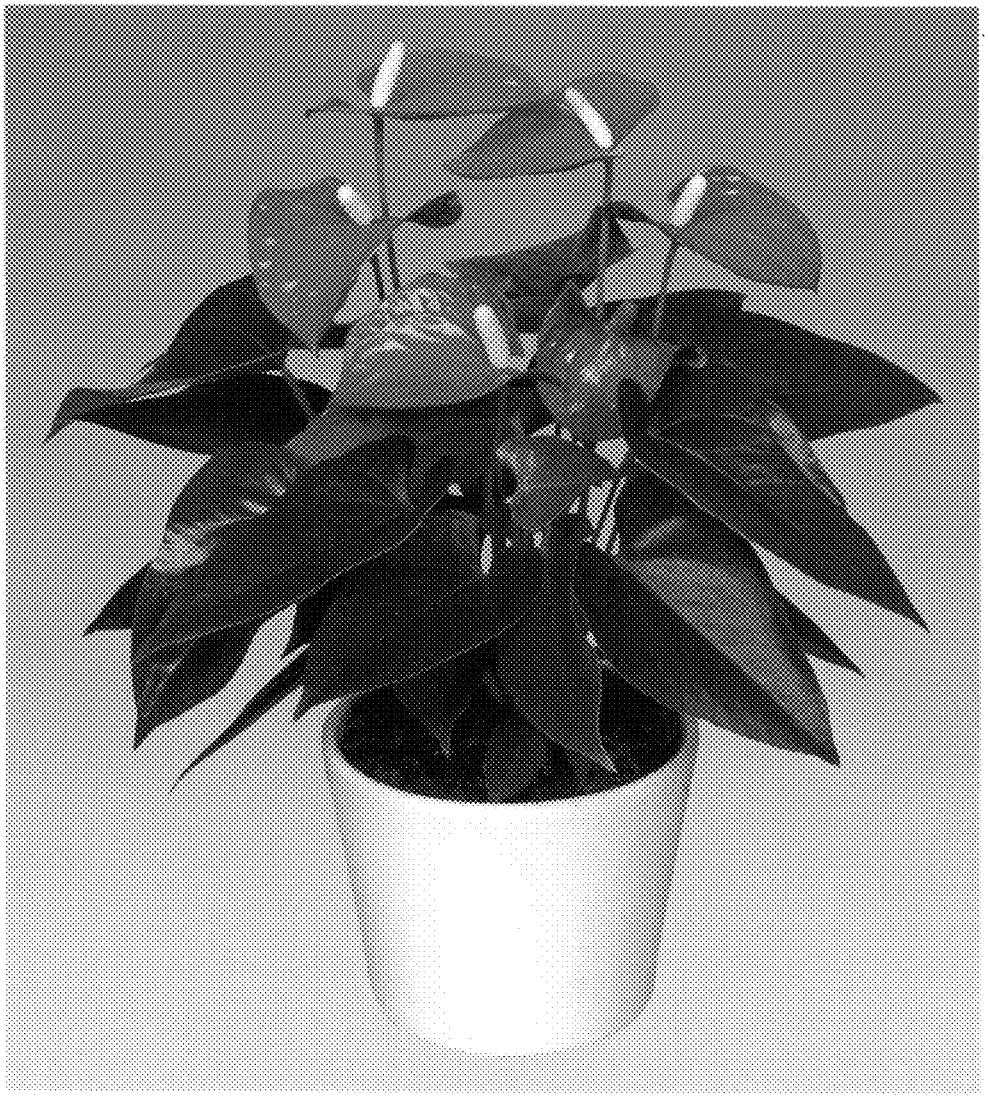
FIG. 1 shows the overall plant habit, including blooms, buds and foliage.
Figure 2:
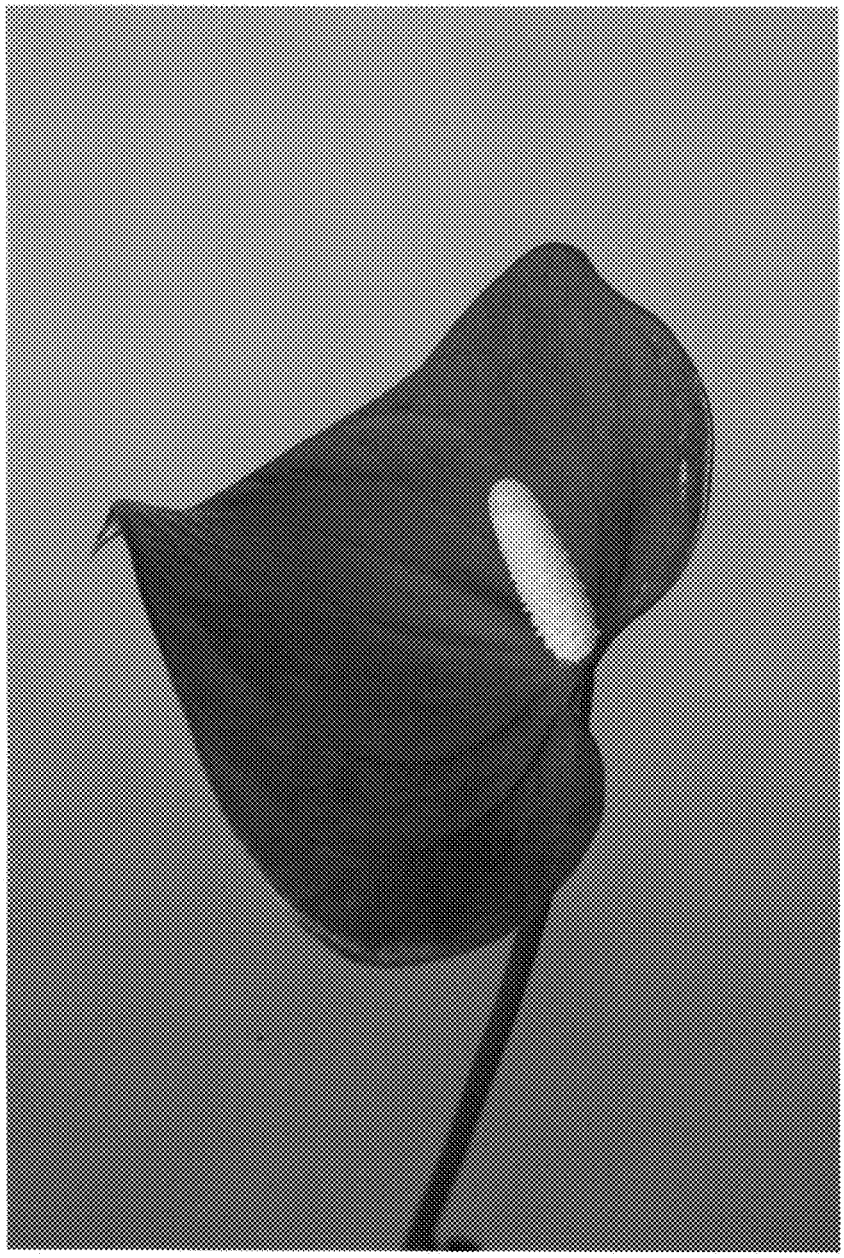
FIG. 2 shows a close-up of the mature spathe.
Figure 3:
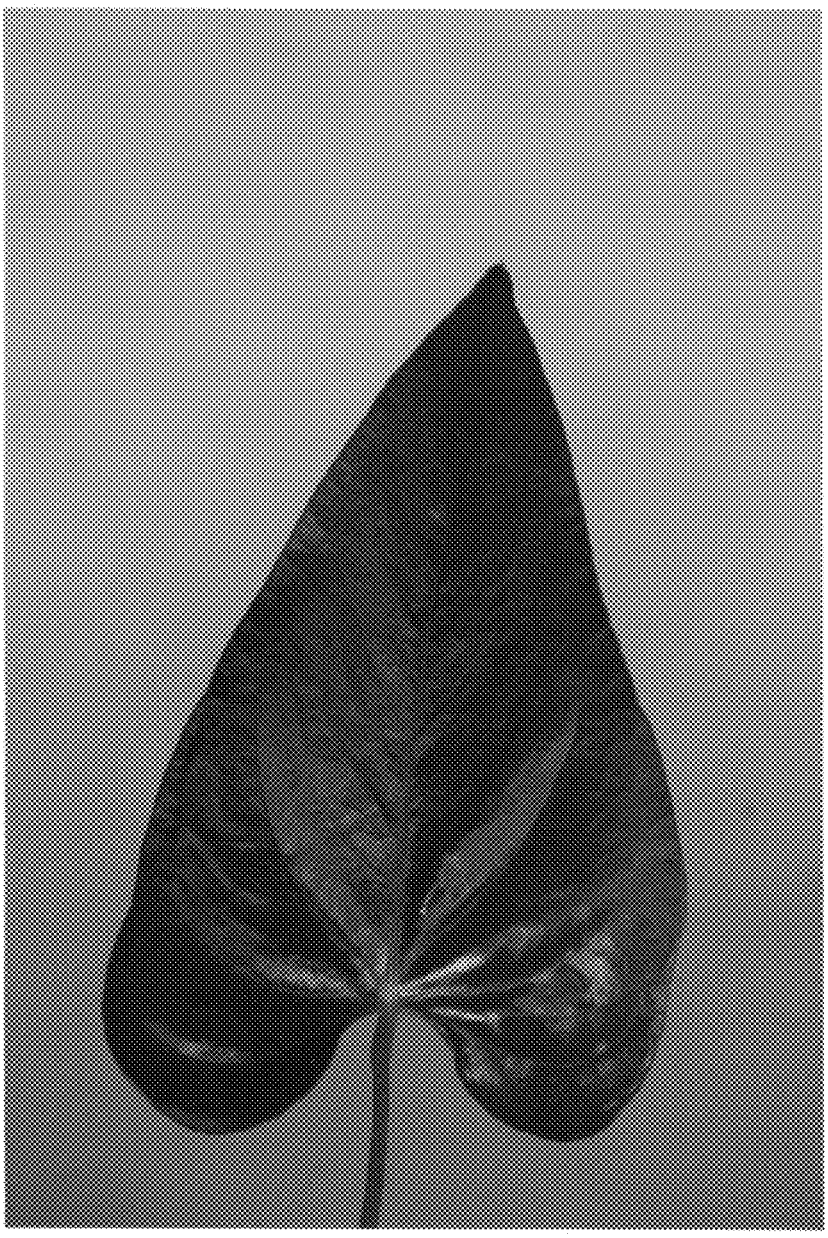
FIG. 3 shows the upper leaf surface.

The following detailed description sets forth the distinctive characteristics of 'ANTHDUNDAL'. The data which define these characteristics were collected from asexual reproductions carried out in Bleiswijk, The Netherlands. The plant history was taken on 45-week old plants which were planted from tissue culture in 12-centimeter pots and grown in a glass greenhouse between 19° C. and 24° C. Observations were made in November 2014. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDUNDAL'.

Parentage:

*Female parent*.—*Anthurium* plant '4110-03' (unpatented).

*Male parent*.—*Anthurium* plant '5442-01' (unpatented).

Plant:

*Propagation*.—Tissue culture.

*Root description*.—Fleshy white-cream colored roots with small hairy lateral roots having yellow-colored root tips.

*Time to produce a finished flowering plant*.—40 to 45 weeks for a 12 cm pot.

*Growth habit*.—Herbaceous perennial.

*Height* (*measured from soil, including inflorescence*) .—24.0 cm to 28.0 cm.

*Width* (*measured from leaf tips*).—30.0 cm to 35.0 cm.

Leaves:

*Immature leaves*.—Length: 6.0 cm to 10.0 cm. Width: 3.0 cm to 6.0 cm. Color: Upper surface: RHS 146A. Lower surface: RHS 146A. Texture (both upper and lower surfaces): Shiny.

*Mature leaves*.—Length (fully expanded): 12.0 cm to 16.0 cm. Width: 7.0 cm to 9.0 cm. Shape: Long ovate. Apex: Acuminate. Base: Cordate. Leaf blade angle with the petiole: Between 100 degrees and 120 degrees. Leaf margin: Entire. Color: Upper surface: RHS 139A. Lower surface: RHS 147A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 147B. Lower surface: RHS 146A.

*Lobes*.—Arrangement: Leaf blade has two small lobes extending past the petiole. The lobes are non-touching. Length of lobes of mature leaf blades: 1.5 cm to 2.5 cm. Width of lobes of mature leaf blades: 3.0 cm to 4.5 cm. Distance from petiole/leaf junction to highest point on lobes of mature leaf blades: 1.5 cm to 2.5 cm.

*Petiole*.—Cross-section: Round. Diameter: 0.3 cm to 0.4 cm. Length: 9.0 cm to 12.0 cm for a mature leaf size. Color: Mature leaf: RHS 146B. Immature leaf: RHS 146C. Cataphyl color surrounding the petiole: Outside: RHS 152A. Inside: RHS 145A.

*Geniculum*.—Length: 1.0 cm to 1.5 cm. Width: 0.4 cm to 0.5 cm. Color: RHS 146C.

Inflorescence:

*Arrangement*.—Single.

*Flowering habit* (*length of flowering season*).—Continuous.

*Number of inflorescences per plant*.—4 to 6 per plant per year.

*Fragrance*.—Absent.

*Longevity of inflorescence on plant*.—Over a year.

*Longevity of the flower as a cut flower*.—Not observed.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 80 degrees and 90 degrees; the spathe stands on a wiry peduncle about 4.0 cm to 7.0 cm above the foliage.

*Shape*.—Cordate and asymmetrical.

*Apex*.—Acuminate.

*Base*.—Auriculate.

*Texture*.—Shiny and slightly blistered.

*Margin*.—Entire.

*Size*.—Height: 14.0 cm to 20.0 cm (peduncle length at maturity). Length: 7.0 cm to 9.0 cm. Width: 7.0 cm to 10.0 cm.

*Color*.—Just fully open: Upper surface: RHS 46A. Lower surface: RHS 47A. This red color remains approximately 25 to 30 weeks after opening. After this period the spathe is limp and dies. The small lobes very slowly accumulate some chlorophyll. The lobes very slowly become green (RHS 146A).

Peduncle:

*Shape*.—Erect.

*Cross-section*.—Round.

*Length*.—14.0 cm to 20.0 cm.

*Diameter*.—0.3 cm to 0.4 cm.

*Color*.—RHS 152C at unrolling of spathe, slowly turning RHS 146B when the spathe matures.

Flowering time:

*General*.—One small rooted untreated tissue culture plant of 2.0 cm tall will flower after 4 to 6 months, depending on the season, and 3 to 4 blossoms will appear. More blossoms appear after some additional weeks so that a full flowering and commercial plant will have 7 to 9 red spathes. Smaller blossoms may occur on less mature plants.

Spadix:

*Size*.—Length: 2.0 cm to 3.0 cm (depending on flower size). Width (at apex): 0.5 cm to 0.6 cm. Width (at base): 0.6 cm to 0.8 cm.

*Shape*.—Columnar.

*Angle from spadix tip to peduncle*.—180 degrees (spadix is in one line with peduncle).

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 15B. Mature: RHS 158B. Ages to: RHS 151A.

Flowers:

*Quantity per spadix*.—100 to 180.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 158B.

Reproductive organs:

*Stamens*.—Not visible.

*Pollen amount*.—Very few.

*Pollen color*.—RHS 156D.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 158B.

*Ovary*.—Rarely visible.

*Ovary color*.—Not measured.

Fruit and seed set: None observed.

COMPARISON WITH PARENTAL AND COMMERCIAL VARIETIES

'ANTHDUNDAL' differs from the female parent plant '4110-03' (unpatented) in that 'ANTHDUNDAL' has a darker green leaf blade with more shine and a darker red spathe color, whereas '4110-03' has a lighter green leaf blade with less shine and a brighter red spathe color. In addition, 'ANTHDUNDAL' has a smaller angle between spadix and spathe, whereas '4110-03' has a bigger angle between spadix and spathe.

'ANTHDUNDAL' differs from male parent plant '5442-01' (unpatented) in that 'ANTHDUNDAL' has a shorter spadix and a darker red spathe color, whereas '5442-01' has a longer spadix and a brighter red spathe color. In addition, 'ANTHDUNDAL' has a leaf blade that is less elliptical cordate, whereas '5442-01' has a leaf blade that is more elliptical cordate.

'ANTHDUNDAL' differs from commercial variety 'ANTHEPEDI' (U.S. Plant Pat. No. 18,644) in that 'ANTHDUNDAL' has a smaller spadix width at the base and a smaller mature leaf size than 'ANTHEPEDI'. In addition, 'ANTHDUNDAL' has a long elliptical cordate shaped leaf blade, whereas 'ANTHEPEDI' has a cordate shaped leaf blade.

'ANTHDUNDAL' differs from commercial variety 'ANTHCOZAM' (unpatented) in that 'ANTHDUNDAL' has a larger spadix width at the base and a larger mature leaf size than 'ANTHCOZAM'. In addition, 'ANTHDUNDAL' has a long elliptical cordate shaped leaf blade and a red spathe, whereas 'ANTHCOZAM' has an elliptical cordate shaped leaf blade and a dark red spathe.

I claim:

1. A new and distinct variety of *Anthurium* plant named 'ANTHDUNDAL', substantially as illustrated and described herein.

* * * * *